(12) United States Patent
Nemori et al.

(10) Patent No.: US 6,485,926 B2
(45) Date of Patent: Nov. 26, 2002

(54) METHOD FOR MEASURING PROTEASE ACTIVITY

(75) Inventors: Ryoichi Nemori, Kanagawa (JP); Koki Nakamura, Kanagawa (JP); Hideaki Naruse, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/742,296

(22) Filed: Dec. 22, 2000

(65) Prior Publication Data

US 2001/0039029 A1 Nov. 8, 2001

(30) Foreign Application Priority Data

Dec. 22, 1999 (JP) ............................................ 11-365074

(51) Int. Cl.⁷ ................................................. C12Q 1/37
(52) U.S. Cl. .......................................... 435/23; 435/18
(58) Field of Search ...................... 435/23, 18

(56) References Cited

U.S. PATENT DOCUMENTS 3,985,620 A * 10/1976 Karges ......................... 435/23
4,931,386 A * 6/1990 Silver et al. .................. 435/23

OTHER PUBLICATIONS

Galis et al. (1995). Microscopic localization of active proteases by in situ zymography: detection of matrix metalloproteinase activity in vascular tissue. FASEB 9. pp. 974–980.*

Komasa–Penkova et al. (1997). Advantages of orange-labeled collagen and gelatine as substrates for rapid collagenase activity measurement. J. Biochem. Biophys. Methods 34, pp. 237–249.*

* cited by examiner

Primary Examiner—Ralph Gitomer
(74) Attorney, Agent, or Firm—Sughrue Mion, PLLC

(57) ABSTRACT

A method for measuring protease activity, which comprises the steps of:

(1) bringing a biosample containing a protease into contact with a crosslinked and/or substantially water-insoluble thin membrane that is formed on a support surface and contains at least one colorant selected from the group consisting of an emulsion-dispersed colorant and a solid-dispersed colorant and a protease substrate; and (2) washing the thin membrane with an aqueous medium and detecting traces of digestion formed on the thin membrane by an action of the protease.

9 Claims, No Drawings

METHOD FOR MEASURING PROTEASE ACTIVITY

BACKGROUND OF THE INVENTION

1. Field of the Invention

The present invention relates to a method for measuring protease. More specifically, the invention relates to a method for measuring protease, which enables accurate diagnosis of malignancy of cancer cells such as infiltrative and metastatic activity, degree of progress of periodontal diseases such as alveolar pyorrhea, destructive pathological conditions in rheumatoid arthritis and the like.

2. Related Art

It is known that various proteases such as matrix metalloproteinases and plasminogen activator are involved in infiltration and metastasis of cancer cells, progress of periodontal diseases such as alveolar pyorrhea, progress of tissue destruction in rheumatoid arthritis and the like, wound healing process, ontogenesis process and the like. As methods for detecting and quantifying such proteases, there are known immunoassay methods which utilize antibodies, immunoblotting methods and electrophoresis zymography methods and the like. Further, as a method for measuring protease activity in tissues, there is known the so-called in situ zymography method, which is disclosed in FASEB Journal, Vol. 9, July, pp.974–980, 1995 or International Patent Publication WO97/32035.

In the method for measuring protease activity disclosed in International Patent Publication WO97/32035, colorants such as Amido black, Coomassie Blue and Ponceau can be used for staining thin membranes such as those of gelatin. However, when the thin membranes are stained with such colorants, tissue slices adhered to the thin membranes are also simultaneously stained. Therefore, it may become difficult to detect traces of digestion, i.e., accurately measure protease activity.

SUMMARY OF THE INVENTION

Therefore, an object of the present invention is to provide means for solving the aforementioned problem. More specifically, the object of the present invention is to provide an improvement that enables more precise analysis of expression of protease activity in the method for measuring protease activity disclosed in International Patent Publication WO97/32035.

The inventors of the present invention conducted various studies to achieve the aforementioned object. As a result, they found that, when a thin membrane containing a protease substrate is colored with a colorant beforehand, the staining step of the thin membrane becomes unnecessary, and expression of protease activity in a tissue or cells on the thin membrane can be analyzed more precisely. Furthermore, they also found that, when cell nuclei are stained with a dye of a color different from that of the colorant contained in the thin membrane, it becomes possible to simultaneously observe information of nuclear morphology and traces of digestion, and thus it becomes markedly easier to detect localization of protease activity. The present invention was achieved on the basis of these findings.

The present invention thus provides a method for measuring protease activity, which comprises the steps of:

(1) bringing a biosample containing a protease into contact with a crosslinked and/or substantially water-insoluble thin membrane that is formed on a support surface and contains at least one colorant selected from the group consisting of an emulsion-dispersed colorant and a solid-dispersed colorant and a protease substrate; and (2) washing the thin membrane with an aqueous medium and detecting traces of digestion formed on the thin membrane by the action of the protease.

According to another aspect of the present invention, there is provided a method for measuring protease activity, which comprises the steps of:

(1) bringing a biosample containing a protease into contact with a crosslinked and/or substantially water-insoluble thin membrane that is formed on a support surface and contains at least one colorant selected from the group consisting of an emulsion-dispersed colorant and a solid-dispersed colorant and a protease substrate;

(2) washing the thin membrane with an aqueous medium and detecting traces of digestion formed on the thin membrane by the action of the protease; and (3) staining the biosample, preferably a tissue slice or cell nuclei, on the thin membrane.

According to a further aspect of the present invention, there is provided a method for measuring protease activity, which comprises the steps of:

(1) bringing one of two or more substantially continuous slices of a biosample into contact with a crosslinked and/or substantially water-insoluble thin membrane that is formed on a support surface and contains at least one colorant selected from the group consisting of an emulsion-dispersed colorant and a solid-dispersed colorant and a protease substrate;

(2) bringing another slice of said slices into contact with a crosslinked and/or substantially water-insoluble thin membrane that is formed on a support surface and contains at least one colorant selected from the group consisting of an emulsion-dispersed colorant and a solid-dispersed colorant, a protease substrate, and a protease inhibitor;

(3) washing the thin membranes with an aqueous medium and detecting traces of digestion formed on the thin membranes by the action of the protease; and (4) comparing the traces of digestion on the thin membrane used in the step (1) with the traces of digestion on the thin membrane used in the step (2).

The present invention further provides a method for measuring protease activity, which comprises the steps of:

(1) bringing one of two or more substantially continuous slices of a biosample into contact with a crosslinked and/or substantially water-insoluble thin membrane that is formed on a support surface and contains at least one colorant selected from the group consisting of an emulsion-dispersed colorant and a solid-dispersed colorant and a protease substrate;

(2) bringing another slice of said slices into contact with a crosslinked and/or substantially water-insoluble thin membrane that is formed on a support surface and contains at least one colorant selected from the group consisting of an emulsion-dispersed colorant and a solid-dispersed colorant, a protease substrate, and a protease inhibitor;

(3) washing the thin membranes with an aqueous medium and detecting traces of digestion formed on the thin membranes by the action of the protease;

(4) staining the biosample, preferably tissue slices or cell nuclei, on the thin membranes,; and (5) comparing the traces of digestion on the thin membrane used in the step (1) with the traces of digestion on the thin membrane used in the step (2).

According to preferred embodiments of these methods of the present invention, there are provided the aforementioned methods wherein cell nucleus staining is performed as the staining of the biosample; the aforementioned methods wherein hematoxylin or Methyl Green is used for the staining of cell nuclei; and the aforementioned methods wherein the biosample is a tissue, a cell, or a body fluid obtained from a mammal including a human. The thin membrane may be crosslinked or contain a hardening agent. The thin membrane may have a monolayer structure or multilayer structure. The thin membrane may contain two or more kinds of colorants, and in a thin membrane having a multiplayer structure, each layer may contain a different colorant.

According to a preferred embodiment of the present invention, there are provided the aforementioned methods wherein the biosample is those isolated and collected from a mammal including a human, preferably a patient, mammal suspected to have a disease, experimental animal or the like. As the biosample, there can be used, solid samples such as tissue pieces, as well as non-solid samples such as samples containing cells or tissue fragment collected from tissues by auction, blood, lymph and saliva. For example, a preferred embodiment of the present invention includes the aforementioned method wherein the biosample is a cancer tissue, lymph node, tissue of periodontal disease, gingival crevicular fluid, tissue or fluid contained in destructive morbid tissues (e.g., synovial fluid of rheumatic morbidity, exudate of alveolar pyorrhea tissue), pleural effusion, ascite, cerebrospinal fluid, mammary gland abnormal secretion fluid, ovarian cystic fluid, renal cystic fluid, pancreatic fluid, sputum, blood or blood cells. In the methods utilizing continuous slices, tissue slices may be used as the biosample. The aforementioned methods wherein the protease is a matrix metalloproteinase or serine protease are preferred embodiments of the present invention.

According to further preferred embodiments, there are provided the aforementioned methods wherein the thin membrane is those containing gelatin or casein; the aforementioned methods wherein the traces of digestion on the thin membrane are stained with a dye distinguishable from the colorant contained in the thin membrane; the aforementioned methods wherein detection of traces of digestion is performed by visual inspection under a microscope; and the aforementioned methods wherein traces of digestion are quantified or numerically represented by using an image processing system. In the methods using a protease inhibitor, the protease inhibitor is preferably a chelating agent, a matrix metalloproteinase inhibitor, or a serine protease inhibitor.

According to a still further aspect of the present invention, there is provided a thin membrane for use in measurement of protease activity, which is a crosslinked and/or substantially water-insoluble thin membrane formed on a support surface and containing at least one colorant selected from the group consisting of an emulsion-dispersed colorant and a solid-dispersed colorant and a protease substrate. This thin membrane can preferably be used for the aforementioned methods.

PREFERRED EMBODIMENTS OF THE INVENTION

The term "measurement method" used in this specification should be construed in its broadest sense including qualitative and quantitative measurements. The methods for measuring protease activity of the present invention are characterized in that a crosslinked and/or substantially water-insoluble thin membrane that contains at least one kind of colorant and a protease substrate is used in the method for measuring a protease which utilizes formation of traces of digestion due to digestion of a protease substrate by a protease contained in a sample (the so-called in situ zymography method: disclosed in, for example, International Patent Publication WO97/32035). This method is characterized in that the substrate and the colorant in the digested portions are washed out by washing of the thin membrane with an aqueous medium, and the presence of protease activity in a sample can be measured by detecting the traces of digestion under a microscope as portions showing lower optical density.

The definition "crosslinked and/or substantially water-insoluble thin membrane" used in the present invention means that, when the thin membrane formed on a support surface is immersed in water at 30° C. for 30 minutes, no trace of protease substrate is substantially dissolved in the water. The thin membrane of the present invention can generally be produced by crosslinking a protease substrate by using a hardening agent. However, a hardening agent may sometimes be not necessarily require. For example, crosslinking of a collagen thin membrane by baking is disclosed in U.S. Pat. No. 4,931,386, and it is also possible to crosslink a protein by using an aminotransferase. In general, an organic or inorganic hardening agent can be used for the production of the thin membrane. Such hardening agents may be appropriately chosen from those available for accelerating curing of gelatin or the like. Hardening agents which do not affect protease activity should be chosen. For example, active halogen compounds (2,4-dichlor-6-hydroxy-1,3,5-triazine and its sodium salt etc.), active vinyl compounds (1,3-bisvinylsulfonyl-2-propanol, 1,2-bis (vinylsulfonylacetamido)ethane, bis(vinylsulfonylmethyl) ether, vinyl polymers having vinylsulfonyl groups on the side chains etc.) may be used, and 1,2-bis (vinylsulfonylacetamido)ethane may preferably be used.

Examples of the proteases particularly preferred for the methods of the present invention include matrix metalloproteinases and serine proteases. These enzymes are explained in detail in "Gan Ten'i No Bunshi Kiko (Molecular Mechanism of Cancer Metastasis)", Ed. By T. Tsuruo, pp.92–107, Medical View Co., Ltd., 1993. Examples of proteases particularly suitable for the methods of the present invention include, for example, matrix metalloproteinases such as interstitial collagenase (MMP-1), gelatinase A (MMP-2) and gelatinase B (MMP-9); serine proteases such as plasminogen activator (PA) and the like. However, target of the methods of the present invention are not limited to these particular proteases.

The protease substrates are not particularly limited so long as they are macromolecular compounds that can be degraded as substrates of proteases. For example, collagen, gelatin, proteoglycan, fibronectin, lamninin, elastin, casein and the like may be used. Preferably, collagen, gelatin, fibronectin or casein may be used, and gelatin or casein may be more preferably used. When gelatin is used, a type of gelatin is not particularly limited. For example, alkali extracted bovine bone gelatin, alkali extracted swine cutis gelatin, acid extracted bovine bone gelatin, phthalation-treated bovine bone gelatin, acid extracted swine cutis gelatin and the like can be used. As the protease substrate, one of the aforementioned substances may be used alone, or two or more of the substances may be used in combination.

By using two or more different protease substrates in combination, a type of a protease contained in a biosample can sometimes be accurately identified. For example, a method may be employed wherein one of two or more substantially continuous slices of a biosample is brought into contact with a thin membrane containing a certain protease substrate, and traces of digestion are detected; and another slice is brought into contact with a thin membrane containing a different protease substrate, and traces of digestion are detected; and then the results obtained are compared. For comparison, two or more kinds of thin membranes each containing a different protease substrate may be used. The thin membrane containing a protease substrate preferably has a thickness of about 1 to 10 $\mu$m, more preferably about 2 to 7 $\mu$m after drying.

The thin membrane of the present invention is formed on a surface of a support. Material and shape of the support are not particularly limited. When surface change on the thin membrane is observed under a microscope, or when the surface change is detected by spectrometric means such as absorption spectrophotometry and fluorometry, for example, the thin membrane is preferably formed on a flat transparent or translucent support. Examples of such a transparent or translucent support include, for example, transparent or translucent plastic films made of polyethylene terephthalate, polyethylene naphthalate, atactic polystyrene, syndiotactic polystyrene, polycarbonate, triacetylcellulose, polymethyl methacrylate, polysulfone, polyarylate and the like. Particularly preferred are polyethylene terephthalate, syndiotactic polystyrene and polyarylate, and most preferred is polyethylene terephthalate. A support to be used itself may be colored.

The thickness of the support is not particularly limited, and the thickness may preferably be from 50 $\mu$m or more to 300 $\mu$m or less, more preferably from 100 $\mu$m or more to 200 $\mu$m or less. A support having a thickness of about 175 $\mu$m is most preferably used. The thin membrane on the support can be formed in a monolayer or multilayer structure. The thin membrane should be prepared so as to have a surface as uniform as possible.

For the preparation of the thin membrane, for example, given amounts of a hardening agent and a solution or dispersion of a colorant can be added to an aqueous solution of a protease substrate and mixed uniformly, and the resulting solution or dispersion can be coated onto a surface of a support and dried. As methods for coating, dip coating method, roller coating method, curtain coating method, extrusion coating method and the like can be employed. However, methods for preparing the thin membrane are not limited to these examples, and methods conventionally used for the preparation of thin membranes in the field of photographic films, for example, may be appropriately employed.

When a thin membrane is formed on a support, an undercoat layer may be provided between the thin membrane and the support to improve the adhesion of the thin membrane and the support. For example, the undercoat layer may be formed by using a polymer or a copolymer obtained by polymerization of one or more monomers selected from vinyl chloride, vinylidene chloride, butadiene, styrene, methacrylic acid, acrylic acid, itaconic acid, maleic anhydride and the like, or a polymer such as polyethyleneimine, epoxy resin, grafted gelatin, nitrocellulose and the like. When a polyester support is used, adhesion between the support and the thin membrane may sometimes be improved by subjecting the surface of the support to corona discharge treatment, ultraviolet irradiation, or glow discharge treatment instead of providing the undercoat layer. By subjecting the support to corona discharge treatment, ultraviolet irradiation, or glow discharge treatment and then applying an undercoat layer, the adhesion between the support and the thin membrane may also be improved.

The phrase "a thin membrane formed on a support surface" and synonyms thereof used in the present specification should not be construed to exclude those with one or more undercoat layers and/or surface treatment of the support. However, means for improving the adhesion of the thin membrane and the support is not limited to those mentioned above, and for example, those widely used in the field of photographic films and the like can be appropriately used. When the thin membrane is formed by laminating a plurality of layers, an intermediate layer can further be provided between two laminated layers, and the membranes are not limited to those wherein laminated two layers are in direct contact. Means for appropriately providing such intermediate layers are generally used, for example, in the field of photographic films and the like. It is also preferable to provide a protective layer on a membrane formed on a support surface, and such a protective layer is commonly used in the field of photographic films and the like.

The colorants added to the thin membrane of the present invention is not particularly limited so long as they have absorption in a visible region, and various compounds including known substances can be used. One kind of colorant may be used, or two or more kinds of colorants may be used in combination. For example, when a laminated thin membrane is used, each layer may contain a colorant of different color. As the coloring manner used for the present invention, it is preferable to use a colorant other than fluorescent colorants. The amount of a colorant added to the thin membrane is not particularly limited, and the amount is generally 0.001 to 10 mmol/m$^2$, preferably 0.01 to 1 mmol/m$^2$, as a total amount of a colorant for unit area of the thin membrane.

Examples of the colorant include, for example, azo colorants (azo lake colorants, insoluble monoazo colorants, insoluble dis-azo colorants, condensed azo colorants, metal complex azo colorants, chelate azo colorants), azomethine colorants, indoaniline colorants, benzoquinone colorants, naphtoquinone colorants, anthraquinone colorants, diphenylmethane colorants, triphenylmethane colorants, xanthene colorants, acridine colorants, azine colorants, oxazine colorants, thiazine colorants, oxonol colorants, melocyanine colorants, cyanine colorants, arylidene colorants, stilyl colorants, perinone colorants, indigo colorants, thioindigo colorants, quinoline colorants, nitro colorants, nitroso colorants, polycyclic colorants (perylene and perinone colorants, quinacridone colorants, dioxazine colorants, isoindolinone colorants, quinophthalone colorants, diketopyrrolopyrrole colorants etc.), and azine colorants as well as other colorants such as alizarin lake colorants, alkali blue, ultramarine and cobalt blue and the like.

Specific compounds are described in "Shinban Senryo Binran (Dye Handbook, New Edition)", edited by The Society of Synthetic Organic Chemistry, Japan, Maruzen, 1970); "Color Index", The Society of Dyers and Colourists; "Shikizai Kogaku Handbook (Color Material Engineering Handbook)", edited by Japan Society of Color Material, Asakura Shoten, 1989; "Insatsu Ink Gijutsu (Printing Ink Technology)", CMC Shuppan, 1984; W. Herbst and K. Hunger, Industrial Organic Pigments, VCH Verlagsgesellschaft, 1993 and the like. Among them, oil-soluble colorants are preferred since they do not adversely affect the enzymatic reaction.

Specific examples of the colorants that can be added to the thin membrane of the present invention are shown below. However, the thin membrane of the present invention is not limited to those utilizing the following colorants.

MD-01
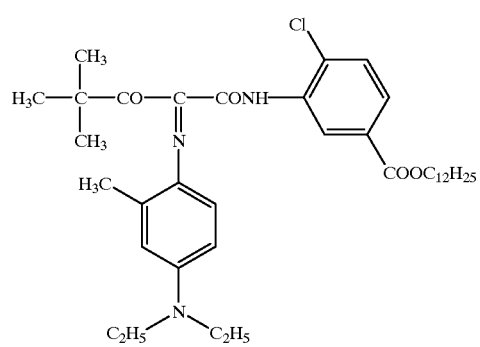
MD-02
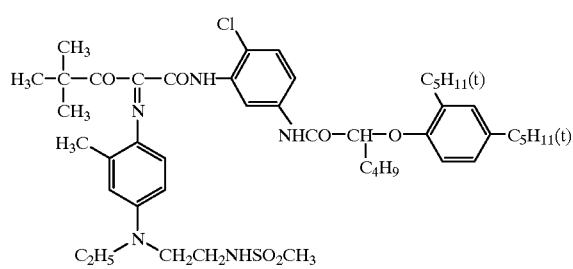
MD-03
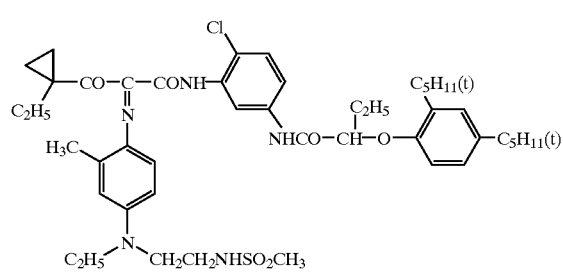
MD-04
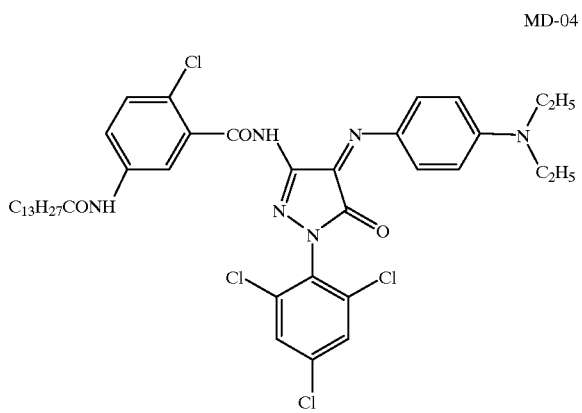
MD-05
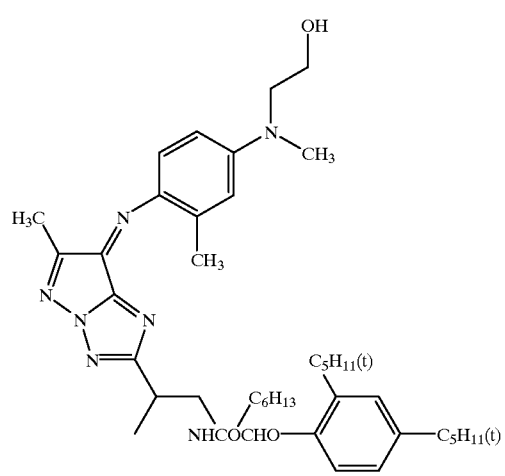
MD-06
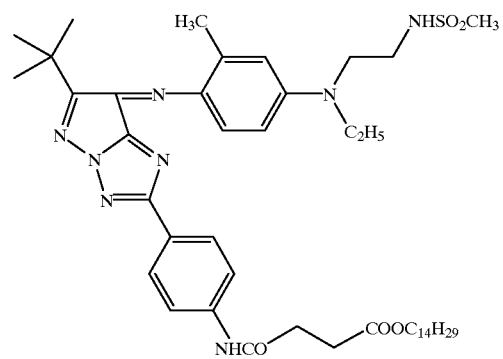
MD-07
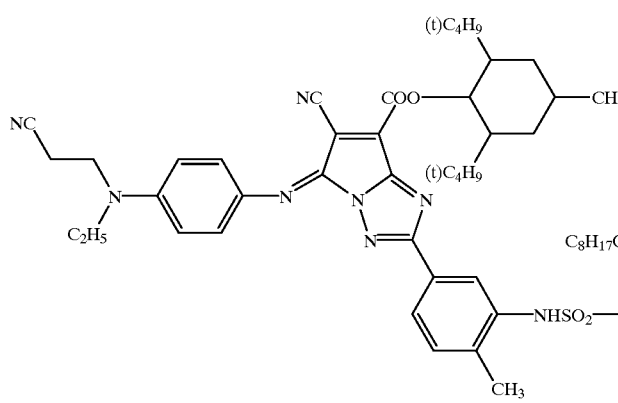

-continued
MD-08
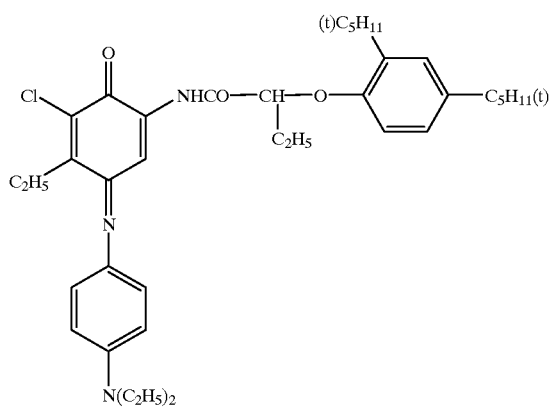
MD-09
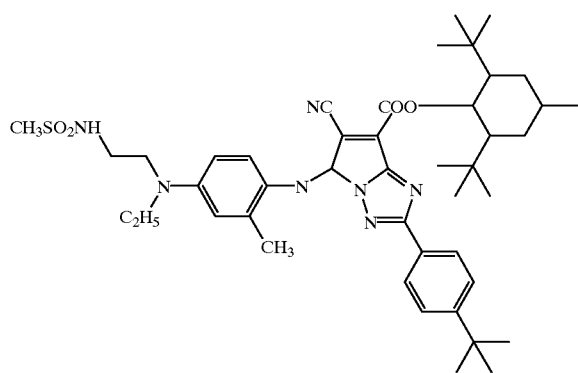
MD-10
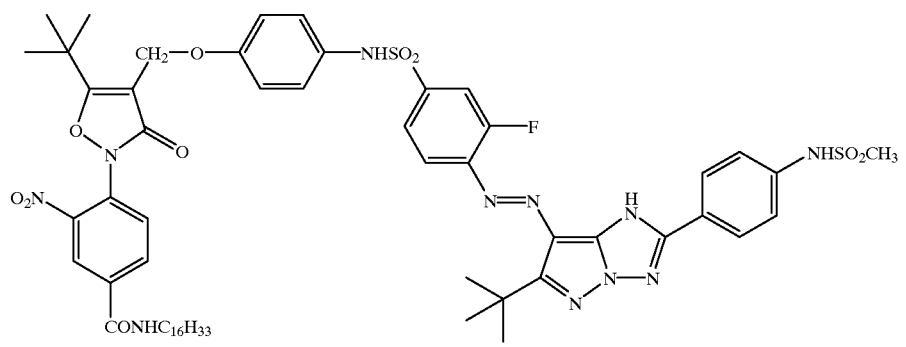
MD-11
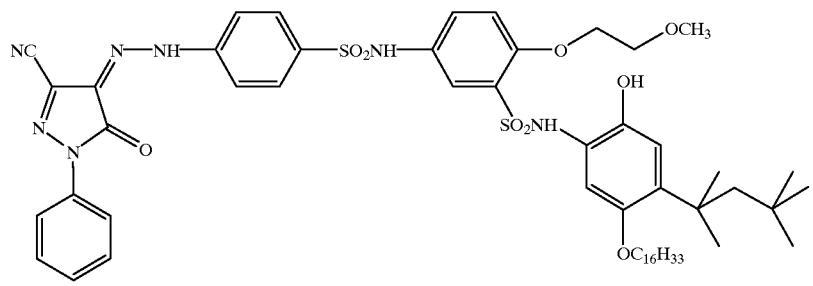
MD-12
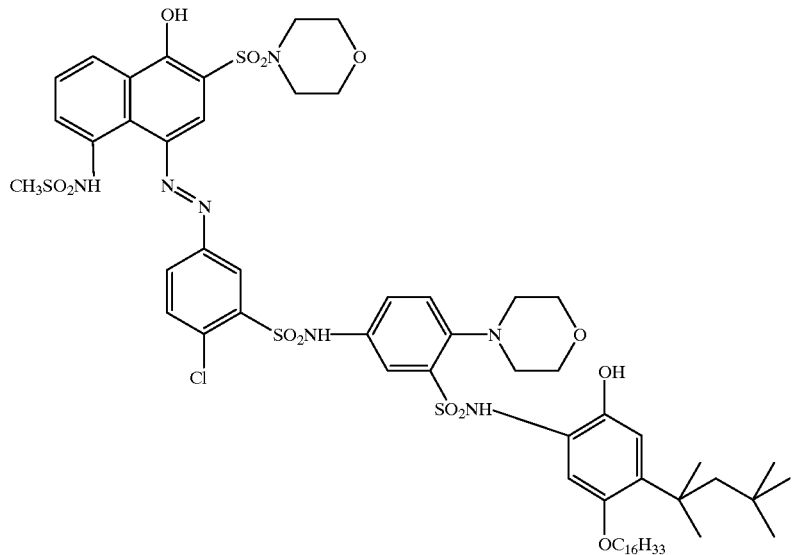

-continued
MD-13
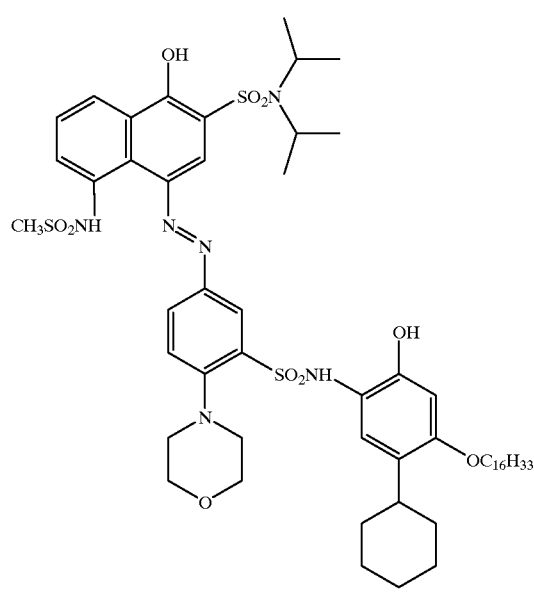
MD-14
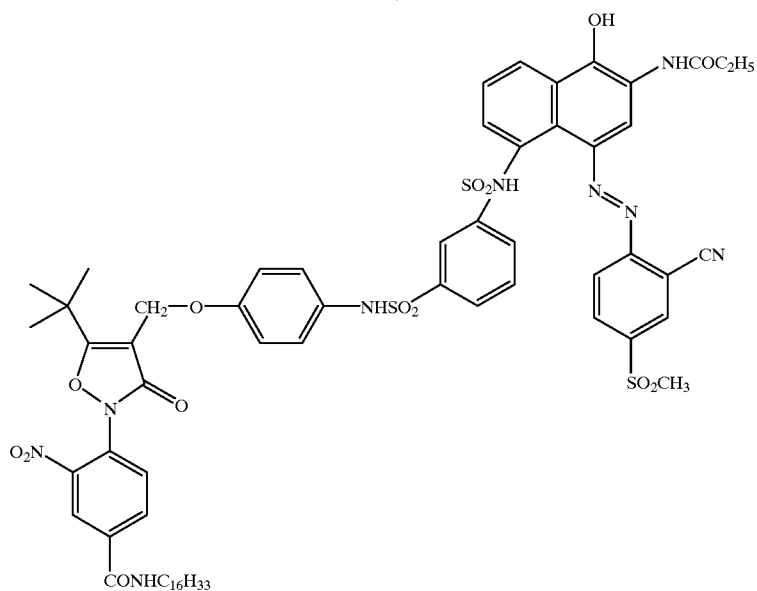
MD-15
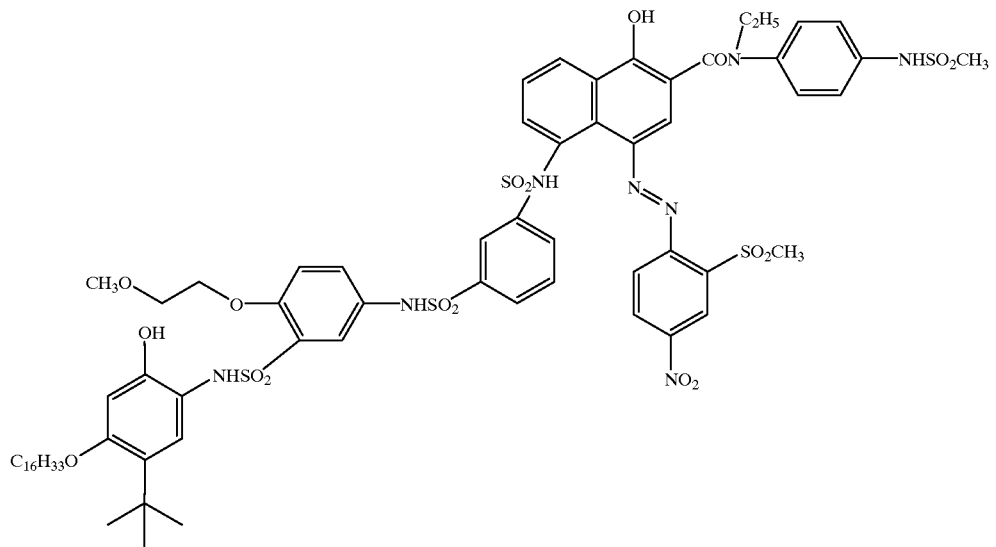

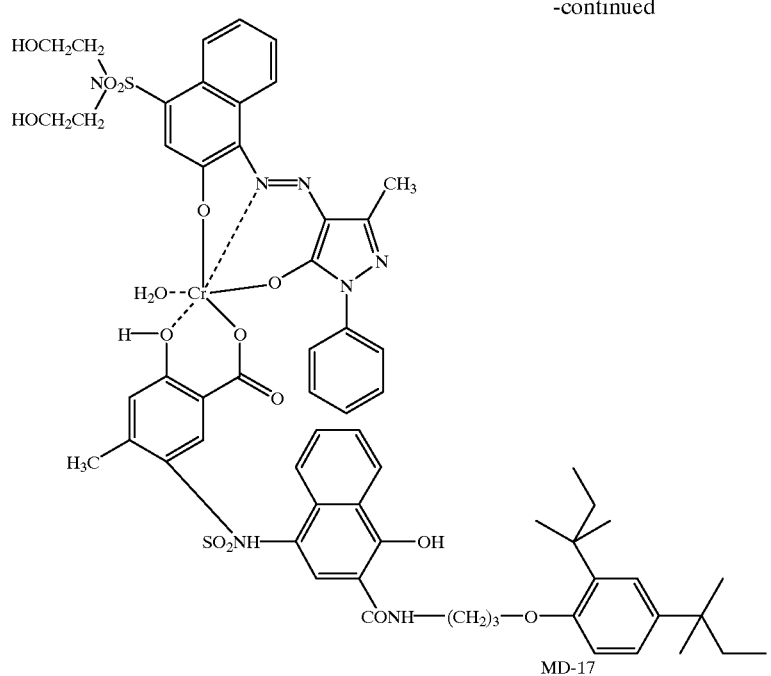
MD-16
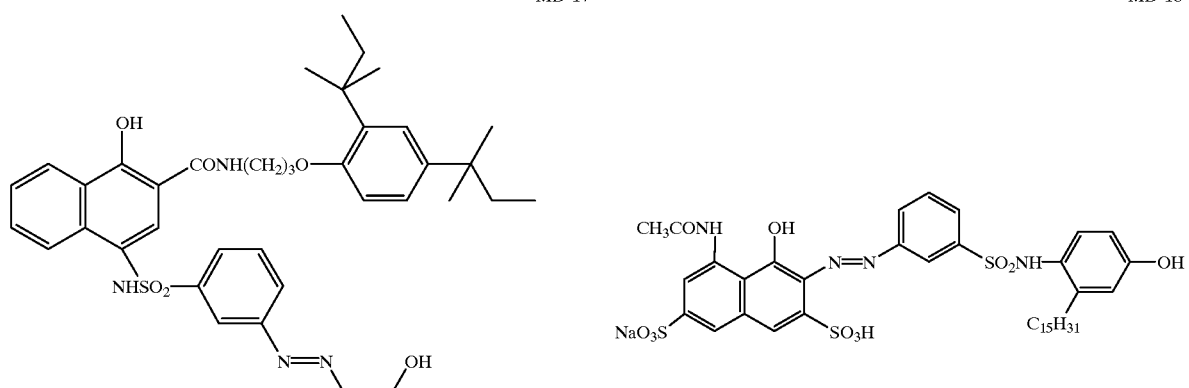
MD-17
MD-18
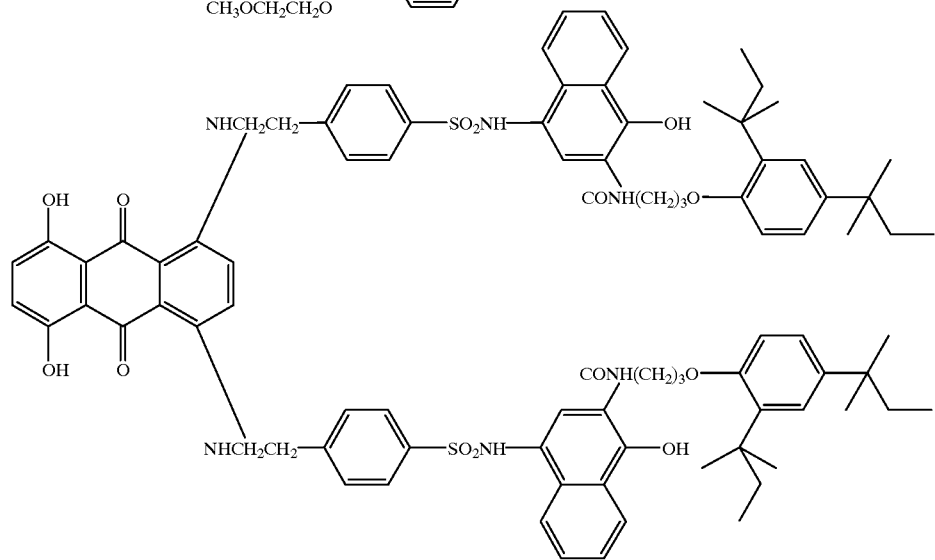
MD-19

-continued
MD-20
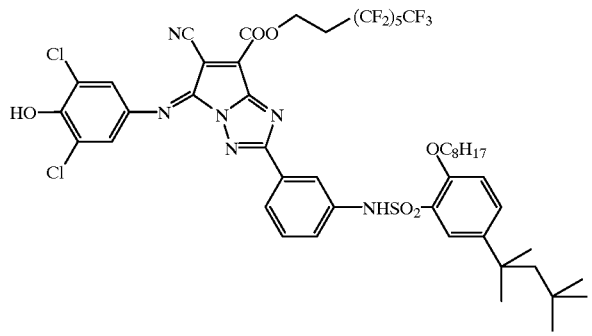
MD-21
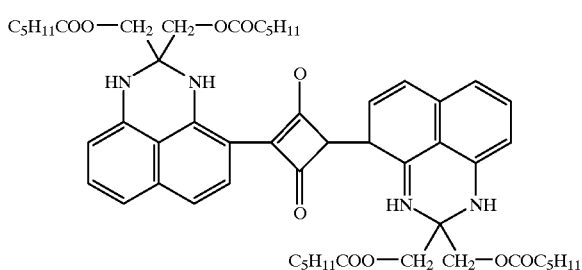
MD-22
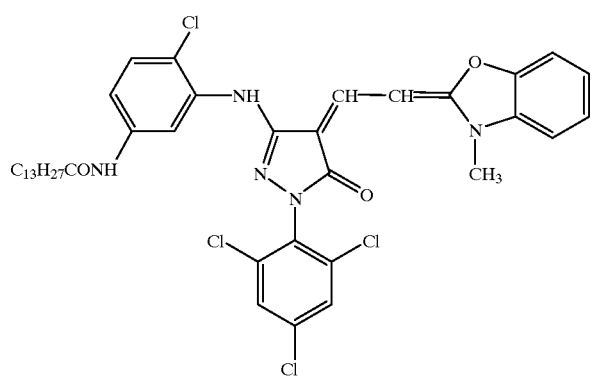
MD-23
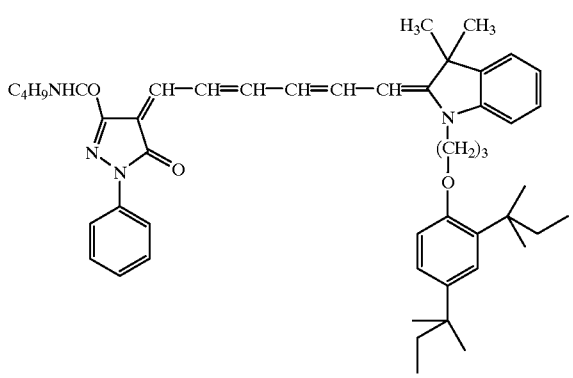
MD-24
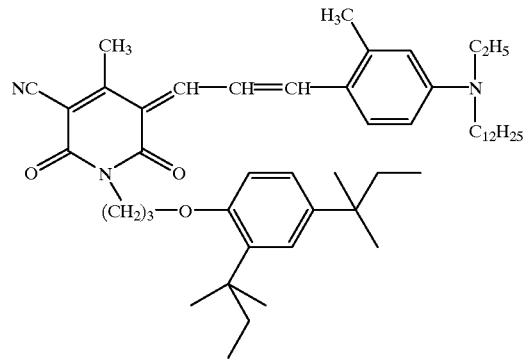
MD-25
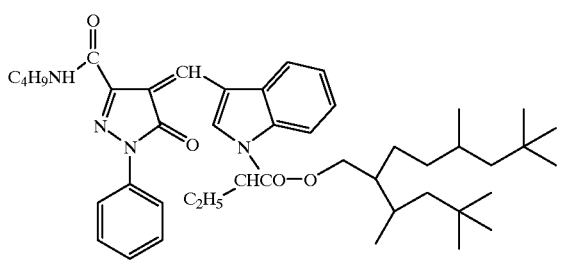
MD-26
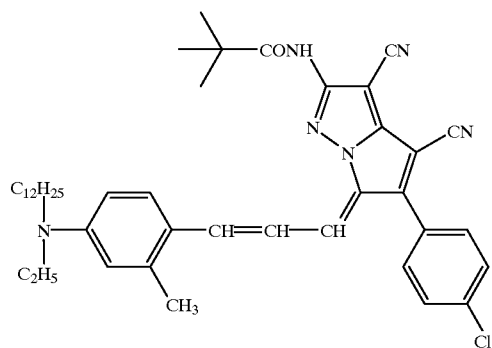
MD-27
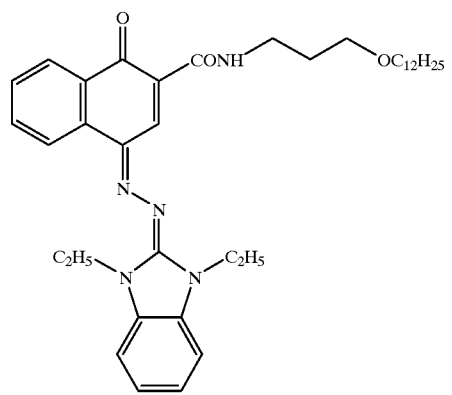

MD-28

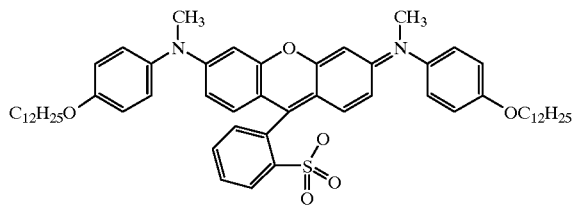

MD-29

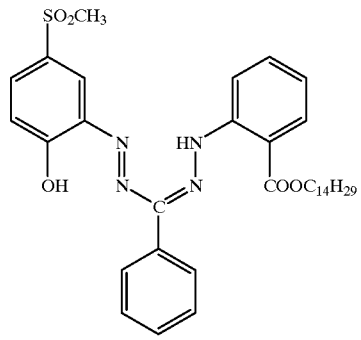

Although the aforementioned colorants, per se, may be used for the manufacture of the thin membrane of the present invention, solid dispersed-colorants subjected to a surface treatment may also be used. Examples of methods for the surface treatment include, for example, methods of surface coating with a resin or wax, methods of adhering a surface active agent, methods of binding a reactive substance (for example, silane coupling agents, epoxy compounds, polyisocyanates etc.) to surfaces of solid-dispersed colorants and the like, and specific means for the surface treatment are described in "Kinzoku Sekken No Seishitsu To Oyo (Properties and Applications of Metal Soap)", Saiwai Shobo; "Insatsu Ink Gijutsu (Technology of Printing Ink)", CMC Shuppan, 1984; "Saishin Ganryo Oyo Gijutsu (Newest Pigment Applied Technology)", CMC Shuppan, 1986 and the like.

For the manufacture of the thin membrane, it is generally desirable to disperse a colorant in the protease substrate, and a dispersing agent call be used for this purpose. The kind of the dispersing agent is not particularly limited, and various dispersing agents can be used depending on the combination of the protease substrate and the colorant to be used. For example, surfactant-type low molecule dispersing agents, macromolecule-type dispersing agents and the like may be used. When the dispersing agent is used in a hydrophobic protease substrate, it is preferred to use a macromolecule-type dispersing agent from a standpoint of dispersion stability. Examples of the dispersing agent include those disclosed in Japanese Patent Unexamined Publication No. 3-69949/1991, EP-A-549486 and the like.

The particle size of the dispersed colorant used for the manufacture of the thin membrane of the present invention is, for example, preferably in the range of 0.01 to 10 μm, more preferably in the range of 0.05 to 1 μm, after dispersion. As the methods for solid-dispersing the colorant in the protease substrate, known dispersion techniques used for the manufacture of inks or toners can be used. Examples of dispersing machines include, for example, sand mill, attriter, pearl mill, super mill, ball mill, impeller, disperser, KD mill, colloid mill, dynatron, three-roll mill, pressurized kneader and the like, and details of the techniques are described in "Saishin Ganryo Oyo Gijutsu (Newest Pigment Applied Technology)", CMC Shuppan, 1986.

In the thin membrane of the present invention, a colorant can be added as solid microparticle dispersion. Such a solid microparticle dispersion of a colorant can be prepared by using a dispersing machine such as a ball mill, a vibration ball mill, a planetary ball mill, a sand mill, a colloid mill, a jet mill, and a roller mill, and using a suitable solvent (water, alcohol etc.) as required. The dispersion is preferably prepared by using a vertical or horizontal-type medium dispersing machine. The dispersion can also be obtained by a method comprising dissolving a colorant in a suitable solvent and adding the solution to a poor solvent for the dye to cause deposition of the dye as microcrystals, a method comprising first dissolving a colorant by controlling pH, and then changing pH to cause deposition of the dye as microcrystals and the like. In any case, it is preferable to use a dispersing agent.

A thin membrane containing solid microparticle dispersion of a colorant can be formed by dispersing solid microparticles of a colorant obtained as described above in a suitable protease substrate to prepare a substantially homogenous solid microparticle dispersion and applying this dispersion on a desired support. Further, another employable method comprises applying a colorant in a dissociated state in the form of salt as an aqueous solution and coating acidic gelatin thereon to simultaneously obtain deposition and dispersion. As the dispersing agent, for example, known anionic, cationic, nonionic or amphoteric low molecule or macromolecule dispersing agents can be used. Examples include the dispersing agents disclosed in Japanese Patent Unexamined Publication No. 52-92716/1977, International Patent Publication WO88/04794, and Japanese Patent Unexamined Publication No. 10-20496/1998. It is particularly preferable to use an anionic and/or nonionic-type macromolecule dispersing agent.

The colorant contained in the thin membrane of the present invention may be used in combination with ultraviolet absorbers disclosed in Japanese Patent Unexamined Publication Nos. 62-215272/1987 (page 125, upper right column, line 2 to page 127, lower left column, last line), 2-33144/1990 (page 37, lower right column, line 14 to page 38, upper left column, line 11), EPO.0.355.600A2 (page 85, lines 22–31), and anti-fading agents disclosed in Japanese Patent Unexamined Publication No. 07-104448/1995 (column 70, line 10 to column 71, line 2).

The colorant can be introduced into the thin membrane as emulsion-dispersed colorant by various known dispersion methods such as the methods disclosed in Japanese Patent Unexamined Publication No. 07-104448/1995 (column 71, line 3 to column 72, line 11) and the like. The oil-in-water dispersion method may also be employed, in which a colorant is dissolved in an organic solvent having a high boiling point (an organic solvent having a low boiling point may be used in combination, as required), then emulsion-dispersed in an aqueous solution of a protease substrate such as gelatin. Examples of the organic solvent having a high boiling point used for the oil-in-water dispersion method are described in U.S. Pat. No. 2,322,027 and the like. Further, the latex dispersion method as one of the polymer dispersion methods and examples of latex are disclosed in U.S. Pat. No. 4,199,363, West German patent application (OLS) Nos. 2,541,274 and 2,541,230, Japanese Patent Publication No. 53-41091/1988, European Patent Publication No. 029104 and the like, and they can be used for the manufacture of the thin film of the present invention. The dispersion method using an organic solvent-soluble polymer is disclosed in International Patent Publication WO88/00723.

Examples of the organic solvent having a high boiling point that can be used for the oil-in-water dispersion method include, for example, phthalic acid esters (for example, dibutyl phthalate, dioctyl phthalate, dicyclohexyl phthalate, di-2-ethylhexyl phthalate, decyl phthalate, bis(2,4-di-tert-amylphenyl) isophthalate, bis(1,1-diethylpropyl) phthalate), esters of phosphoric acid or phosphonic acid (for example, diphenyl phosphate, triphenyl phosphate, tricresyl phosphate, 2-ethylhexyl diphenyl phosphate, dioctyl butyl phosphate, tricyclohexyl phosphate, tri-2-ethylhexyl phosphate, tridodecyl phosphate, di-2-ethylhexyl phenyl phosphate), benzoic acid esters (for example, 2-ethylhexyl benzoate, 2,4-dichlorobenzoate, dodecyl benzoate, 2-ethylhexyl p-hydroxybenzoate), amides (for example, N,N-diethyl-dodecaneamide, N,N-diethyl-laurylamide), alcohols or phenols (isostearyl alcohol, 2,4-di-tert-amylphenol etc.), aliphatic esters (for example, dibutoxy-ethyl succinate, di-2-ethylhexyl succinate, 2-hexyldecyl tetradecanoate, tributyl citrate, diethyl azelate, isostearyl lactate, trioctyl citrate), aniline derivatives (N,N-dibutyl-2-butoxy-5-tert-octylaniline etc.), chlorinated paraffins (paraffins having a chlorine content of 10% to 80%), trimesic acid esters (for example, tributyl trimesicate), dodecylbenzene, diisopropylnaphthalene, phenols (for example, 2,4-di-tert-amylphenol, 4-dodecyloxyphenol, 4-dodecyloxycarbonylphenol, 4 (4-dodecyloxyphenylsulfonyl)phenol), carboxylic acids (for example, 2-(2,4-di-tert-amylphenoxybutyric acid, 2-ethoxyoctanedecanoic acid), alkylphosphoric acid (for example, di-2-(ethylhexyl)phosphoric acid, diphenylphosphoric acid) and the like. An organic solvent having a boiling point of 30° C. to about 160° C. (for example, ethyl acetate, butyl acetate, ethyl propionate, methyl ethyl ketone, cyclohexanone, 2-ethoxyethyl acetate, dimethylformamide) may be used in combination as an auxiliary solvent.

The amount of the organic solvent having a high boiling point may be 10 g or less, preferably of 5 g or less, more preferably 1 g to 0.1 g, for 1 g of a colorant used. For 1 g of the protease substrate, the amount may suitably be 1 ml or less, preferably 0.5 ml or less, more preferably 0.3 ml or less. When a hydrophobic colorant is dispersed in hydrophilic colloids, various surface active agents can be used. For example, those mentioned in Japanese Patent Unexamined Publication No. 59-157636/1984, pages 37–38 and Research Disclosure (abbreviated as RD hereinafter in the specification) 17643 as surface active agents can be used.

Various kinds of additives may be added to the thin membrane as required, besides the protease substrate, the colorant, and the hardening agent. Examples of the additives include surface active agents for facilitating application of the thin membrane, oils or emulsifiers for dispersing the colorant, preservatives, fungicides, acids or bases for controlling pH, inorganic ions such as Ca++ for controlling enzyme activity and the like. However, additives are not limited to these examples. Antistatic means may also be provided for the thin membrane of the present invention. For example, those having a surface resistivity of $10^{12}$ Ω or less on the side of the protease substrate layer or the opposite side can be preferably used. As means for reducing surface resistivity of the membrane, for example, techniques used for photographic films can be used.

For the manufacture of the thin membrane of the present invention, for example, the following additives can be used as required: hardening agents (RD117643, page 26; RD18716, page 651, left column; RD307105, pages 874–875), binders (RD17643, page 26; RD18716, page 651, left column; RD307105, pages 873–874), plasticizers or lubricants (RD17643, page 27; RD18716, page 650, right column; RD307105, page 876), application aids or surface active agents (RD17643, pages 26–27; RD18716, page 650, right column; RD307105, pages 875–876), antistatic agents (RD17643, page 27; RD18716, page 650, right column; RD307105, pages 876–877), and matting agents (RD307105, pages 878–879). All of these additives are widely used in the field of photographic films, and can be used in the same manner for the manufacture of the thin membrane of the present invention.

As the biosample used for the methods of the present invention, a biosample isolated and collected from a mammal including a human can be used. For example, a biosample isolated and collected from a mammal with a disease, mammal suspected to have a disease, experimental animal or the like can be used. The form of the biosample is not particularly limited, and solid samples such as tissue slices and non-solid samples such as body fluid can be used. Examples of the non-solid samples include samples containing cells or tissue fragments collected from tissues by suction, body fluids such as blood, lymph and saliva. There can be used, for example, cancer tissues isolated and collected from tumor tissues of lung cancer, stomach cancer, esophageal cancer, colon cancer, breast cancer, uterine cancer, ovarian cancer, thyroid cancer, liver cancer, intraoral cancer, prostatic cancer, renal cancer, bladder cancer and the like by surgical operation or histological examination, lymph nodes, tissues of periodontal diseases, tissues such as synovial membranes and bone tissues isolated and collected from tissues of rheumatoid arthritis patients by surgical operation or histological examination, gingival crevicular fluids, fluids contained in destructive morbid tissues (e.g., synovial fluid of rheumatic morbidity, exudate of alveolar pyorrhea tissue), pleural effusions, ascites, cerebrospinal fluids, mammary gland abnormal secretion fluids, ovarian cystic fluids, renal cystic fluids, sputum, blood, blood cells and the like.

When the sample is a tissue, for example, a slice having a thickness of 1 to 10 μm, preferably 2 to 6 μm, may be prepared from a sample rapidly frozen in liquid nitrogen by using an apparatus for preparing frozen sections, and then the slice may be applied to a thin membrane to bring the sample into contact with the thin membrane. A tissue specimen collected by paracentesis and suction may also be rapidly frozen with a molding material such as compounds and made into slices in a similar manner for use. When a non-solid sample containing cells or tissue fragments is used, which is collected from tissues by paracentesis and suction, the sucked sample may be discharged on a thin membrane so that the cells can adhere to the thin membrane in a dispersed state. Further, when the biosample is a piece of tissue, moisture of the collected tissue may be wiped lightly, and then the tissue can be left standing on a thin membrane containing a protease substrate for 1 to 30 minutes for the contact of the sample with the thin membrane.

When a non-solid sample such as synovial fluid collected from a patient with rheumatoid arthritis is used, the sample is diluted to an appropriate concentration and/or subjected to a necessary pretreatment, about 1 to 50 μl, preferably about 1 to 20 μl, of the sample can be dropped onto the thin membrane. When gingival crevicular fluid of periodontal disease is used as a sample, a method is employable wherein a piece of filter paper may be inserted into gingival crevice to collect about 5 to 10 μl of gingival crevicular fluid, and the filter paper may be applied to a thin membrane. After the collection of gingival crevicular fluid, the gingival crevicular fluid may be optionally extracted from the filter paper using distilled water or a suitable buffer (for example, 50 mM Tris-HCl, pH 7.5, 10 mM $CaCl_2$, 0.2 M NaCl), and the extract may be dropped onto a thin membrane, as required. When body fluid that can be collected in a larger amount (cystic fluid etc.) is used, a result with good reproducibility can be obtained by immersing a part of the thin membrane into a vessel containing the sample.

After a sample containing a protease is brought into contact with a thin membrane by adhering a tissue slice containing a protease substrate to the thin membrane, or dropping a liquid sample containing a protease substrate onto the thin membrane or the like, the thin membrane is incubated at a temperature suitable for expression of the protease activity, e.g., 37° C., under a saturated humid condition for a period required for digestion of the substrate. Although the time required for the digestion may vary depending on the kinds of the sample and the thin membrane, the incubation is preferably performed at 37° C. for 1 to 48 hours, more preferably 6 to 30 hours, for a tissue slice or cells obtained by suction or non-solid sample containing tissue fragments, or for 0.5 to 24 hours, more preferably 1 to 16 hours, for a liquid sample such as exudate, to allow formation of traces of digestion on the thin membrane by an action of protease in the sample. Then, the thin membrane is washed with an aqueous medium to remove the digested substrate and colorant contained therein. As the aqueous medium, water as well as a mixture of water and a water miscible organic solvent such as methanol, ethanol, acetone and the like can be used. The traces of digestion can be observed under an optical microscope.

By adhering one of two or more substantially continuous slices of a biosample to a thin membrane not containing a protease inhibitor, and adhering another slice among the remaining slices to a thin membrane containing a protease inhibitor, and then by comparing traces of digestion formed in each of the thin membranes, the kind of the protease can be identified. The kind of the protease inhibitor is not particularly limited, and chelating agents, matrix metalloproteinase inhibitors, serine protease inhibitors and the like can be suitably used.

When a thin membrane consisting of a monolayer is used which contains a protease substrate, a colorant, and a hardening agent if required, optical density of the thin membrane is reduced as the thin membrane is digested by a protease contained in a sample. However, when a thin membrane containing a protease substrate consists of laminated applied layers and a dye of different color is added to each of the layers, the color hue of the thin membrane changes with optical density as the thin membrane is digested by a protease in a sample. If such a thin membrane is used, it is easy to visually determine the strength of the digestion.

By measuring protease activity contained in a biosample using the methods of the present invention, the conditions of the living body from which the sample is derived, for example, metastasis of cancer, progress of rheumatism and the like, can be investigated. For determining the strength of digestion in traces of digestion, any of methods such as a method of judging by visual inspection under an optical microscope, a method of measuring optical density of traces of digestion with a spectrometer, a method of storing an image captured by an optical microscope in a computer and performing various numerical evaluation of the traces of digestion by image analysis techniques and the like. When image analysis is performed, various data processing methods can be used, and the kind thereof is not particularly limited. However, it is preferable to numerically evaluate the degree of digestion by using integration of areas of traces of digestion, or integration of densities and areas of traces of digestion.

EXAMPLES

The present invention will be explained more specifically with reference to the following examples. However, the scope of the present invention is not limited to these examples.

Example 1

Preparation of gelatin thin membrane containing red colorant emulsion (Preparation of support)

A clear PET film having a thickness of 175 μm was subjected to a surface corona discharge treatment and used for preparation of a support applied with undercoats composed of the following compositions. Electric resistivity of the back face was measured as $1 \times 10^8$ Ω.

| 1. Front surface | |
| --- | --- |
| Gelatin | 0.3 g/m² |
| Hardening agent (1) | 0.001 g/m² |
| 2. Back surface | |
| Gelatin | 0.05 g/m² |
| Aqueous dispersion of stannic oxide doped with antimony oxide | 0.04 g/m² |
| Methylcellulose | 0.01 g/m² |
| Matting agent (PMMA polymer particles having average diameter of 3 μm) | 0.005 g/m² |
| Hardening agent (2) | 0.002 g/m² |

-continued

| Hardening agent (1) | Hardening agent (2) |
|---|---|
| $\left[\mathrm{HO}\!-\!\!\underset{\underset{O}{\|}}{\overset{O}{\|}}{C}\!-\!(CH_2)_4\!-\!\overset{O}{\underset{\|}{C}}\!-\!NH(CH_2)_2\!-\!\overset{H}{\underset{\substack{\|\oplus \\ CH_2 \\ | \\ CHOH \\ | \\ CH_2Cl}}{N}}\!-\!(CH_2)_2\!-\!NH\!\right]_n\!\!H \quad Cl^{\ominus}$ | $\underset{\substack{N \\ \|}}{NaO}\!\!-\!\!\underset{N}{\overset{N}{\bigtriangleup}}\!\!-\!\!Cl$ on triazine with Cl |

(Preparation of colorant coating solution)

11.8 g of Colorant compound (MD-06), 3.9 g of Colorant compound (MD-1), 15.7 g of solvent (Solv-1) and 50 ml of ethyl acetate were admixed to form a solution, and this solution was added to 270 ml of 10 wt % aqueous solution of gelatin (Sigma, bloom value: 175) containing 8 ml of sodium dodecylbenzenesulfonate (Surface active agent (1)), and then emulsion-dispersed by an ultrasonic homogenizer. 2740 g of 10 wt % gelatin (Sigma, #2625) was added to the resulting dispersion and dissolved to prepare a coating solution for the first layer. Coating solutions for layers other than the first layer were prepared in the same manner, and coated on the aforementioned support in a structure shown in Table 1 to form a thin membrane.

Example 2

Preparation of gelatin thin membrane containing red colorant emulsion and chelating agent A thin membrane was prepared in the same manner as in Example 1 except that o-phenanthroline (Wako Pure Chemicals) and Surface active agent (3) were added to the first layer (colored layer) of Example 1 in such amounts that the coated amounts became 0.78 g/m$^2$ and 0.06 g/m$^2$, respectively.

Example 3

Preparation of gelatin thin membrane comprising multiple layers each containing emulsion of a colorant of different color In the same manner as in Example 1, dispersions of yellow, magenta and cyan colorants were prepared, and a

TABLE 1

| Layer No. | Additive | Coated amount (g/m$^2$) |
|---|---|---|
| Second layer (Protective layer) | Gelatin | 0.30 |
| | Surface active agent (2) | 0.09 |
| | Hardening agent (3) | 0.04 |
| First layer (Colored layer) | Colorant compound (MD-06) | 0.19 |
| | Colorant compound (MD-01) | 0.07 |
| | Solvent (Solv-1) | 0.26 |
| | Gelatin | 5.00 |
| | Surface active agent (1) | 0.07 |
| | Surface active agent (3) | 0.02 |
| Support | | |
| (PET base of 175 μm, resistivity of back face: 1 × 10$^8$ Ω) | | |

Surface active agent (2)

Hardening agent (3)

$H_2C\!=\!CH\!-\!SO_2\!-\!CH_2\!-\!SO_2\!-\!CH\!=\!CH_2$

Surface active agent (3)

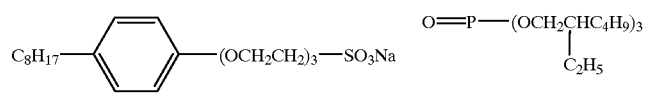

Solv-1

$O\!=\!P\!-\!(OCH_2CHC_4H_9)_3$
$\quad\quad\quad |$
$\quad\quad\quad C_2H_5$ thin membrane was prepared to have the structure shown in Table 2.

TABLE 2

| Layer No. | Layer name | Additive | Coated amount (g/m²) |
|---|---|---|---|
| Fourth layer | Protective layer | Gelatin | 0.387 |
| | | Matting agent (PMMA resin) | 0.017 |
| | | Surface active agent (2) | 0.006 |
| | | Surface active agent (3) | 0.020 |
| | | Hardening agent (1) | 0.048 |
| Third layer | Cyan color layer | Gelatin | 2.000 |
| | | Cyan colorant | 0.160 |
| | | High boiling point solvent (Solv-1) | 0.160 |
| | | Surface active agent (1) | 0.043 |
| Second layer | Magenta color layer | Gelatin | 2.000 |
| | | Magenta colorant | 0.164 |
| | | High boiling point solvent (Solv-1) | 0.164 |
| | | Surface active agent (1) | 0.044 |
| First layer | Yellow color layer | Gelatin | 2.000 |
| | | Yellow colorant | 0.386 |
| | | High boiling point solvent (Solv-1) | 0.386 |
| | | Surface active agent (1) | 0.090 |
| | | Support (PET base of 175 μm, resistivity of back surface: 1 × 10⁸ Ω) | |

Example 4
Preparation of gelatin thin membrane comprising multiple layers each containing an emulsion of a colorant of different color and a chelating agent A thin membrane was prepared in the same manner as in Example 3 except that o-phenanthroline (Wako Pure Chemicals) and Surface active agent (3) were added to the first, second and third layers of Example 3 in such amounts that the coated amount became 0.31 g/m² and 0.02 g/m², respectively.

Example 5
Preparation of thin membrane containing a water-soluble red colorant
(Preparation of a colorant solution)

A colorant solution prepared by dissolving 2.0 g of Colorant compound (MD-36) in 100 ml of water was dissolved in 500 ml of 10 wt % gelatin (Sigma, #2625) solution at 40° C. to form a colorant solution. By using this solution, a thin membrane shown in Table 3 was prepared.

TABLE 3

| Layer No. | Additive | Coated amount (g/m²) |
|---|---|---|
| First layer (Colored layer) | Colorant compound (MD-06) | 0.20 |
| | Gelatin | 5.00 |
| | Support (PET base of 175 μm, resistivity of back surface 1 × 10⁸ Ω) | |

Example 6
Measurement of protease activity using gelatin thin membrane containing red colorant emulsion A frozen breast cancer specimen extracted by surgical operation was sliced at −25° C. into a slice having a thickness of 4 μm by using an apparatus for preparing frozen sections and adhered to a gelatin thin membrane containing red colorant emulsion prepared according to Example 1. This membrane was incubated at 37° C. for 16 hours under 100% of relative humidity, air-dried, and washed with water for 10 minutes. The membrane was immersed in a Mayer's hematoxylin solution for 2 minutes for nuclear staining, washed with water for 10 minutes, immersed in ethanol for 20 seconds, and then air-dried. After the drying, a Cover Aid Film (Sakura Seiki Co., Ltd.) was adhered to the membrane by using xylene so that the film covered the tissue slice to encapsulate the breast cancer slice. When this film was held on a plastic mount and observed under an optical microscope, gelatin digestion was observed on sites contacting with the breast cancer tissue slice where the cancer cells were considered to be present based on the morphology of the nuclei, and thus presence of protease activity was verified. Although the cell nuclei in the tissue slice were stained with hematoxylin, the staining did not affect observation of the portions of gelatin digestion, and the nuclei were clearer compared with those in Comparative Example. The operation was simple, because preparation of Ponceau staining solution and staining operation were not required.

Example 7
Measurement of protease activity using gelatin thin membrane containing red colorant emulsion and chelating agent A frozen breast cancer specimen extracted by surgical operation was sliced at −25° C. into a slice having a thickness of 4 μm by using an apparatus for preparing frozen sections and adhered to a gelatin thin membrane containing red colorant emulsion prepared according to Example 2. This membrane was incubated, washed with water, stained with hematoxylin, and then washed with water under the same conditions as in Example 6. When this film was held on a plastic mount and observed under an optical microscope, gelatin digestion observed in Example 6 was substantially completely inhibited. From this result, it was concluded that the gelatin digestion observed in Example 6 was caused by MMP.

Example 8
Measurement of protease activity using gelatin thin membrane comprising multiple layers each containing an emulsion of a colorant of different color A frozen cervical cancer specimen extracted by surgical operation was sliced at −25° C. into a slice having a thickness of 4 μm by using an apparatus for preparing frozen sections and adhered to the gelatin thin membrane comprising multiple layers each containing emulsion of a colorant of different color prepared in Example 3. This membrane was incubated at 37° C. for 16 hours under 100% of relative humidity, air-dried, and then washed with water for 10 minutes. The membrane was immersed in a Mayer's hematoxylin solution for 2 minutes for nuclear staining, washed with water for 10 minutes, immersed in ethanol for 20 seconds, and then air-dried. After the drying, a Cover Aid Film (Sakura Seiki Co., Ltd.) was adhered to the membrane by using xylene so that the aim covered the tissue slice to encapsulate the cervical cancer slice. When this film was held on a plastic mount and observed by using an optical microscope, gelatin digestion was observed on sites contacting with the cervical cancer tissue slice where the cancer cells were considered to be present based on the morphology of the nuclei, and thus presence of protease activity was verified. In this experiment, color change was observed in the portions where the gelatin digestion was caused in contrast to the gray color of the whole film. From this result, it was found that, if a gelatin membrane comprising multiple layers each containing emulsion of a colorant of different color was used, protease activity was detectable as change of color hue.

Example 9
Measurement of protease activity using gelatin thin membrane comprising three layers each containing an emulsion of a colorant of different color and a chelating agent A frozen cervical cancer specimen extracted by surgical operation was sliced at −25° C. into a slice having a thickness of 4 μm by using an apparatus for preparing frozen sections and adhered to a gelatin thin membrane containing red colorant emulsion prepared according to Example 4. This membrane was incubated, washed with water, stained with hematoxylin, and then washed with water under the same conditions as in Example 8. When this film was held on a plastic mount and observed under an optical microscope, gelatin digestion observed in Example 8 was substantially completely inhibited. From this result, it was concluded that the gelatin digestion observed in Example 8 was caused by MMP.

Example 10
Preparation of a colorant coating solution 12.0 g of Colorant compound (MD-9) was ground by using a mortar for 30 minutes and added with 100 ml of glass beads of 0.5 mΦ, 3.3 g of Surface active agent (A), and 90 g of water in a 150 ml vessel, and then the mixture was dispersed for 2 hours by using a DYNO-MILL TYPE KDL dispersing machine (Shinmaru Enterprises Corporation).

2740 g of 10 wt % gelatin (Sigma, #2625) was added to the resulting dispersion and dissolved to prepare a coating solution for the first layer. By using the above solution, a thin membrane of the present invention was prepared in the same manner as Example 1.

Evaluation was carried out in the same manner as Example 6 by using the above-obtained thin membrane, and as a result, almost the same advantages were obtained as those in Example 6.

Surface active agent (A)

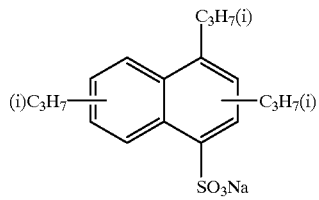

Comparative Example
Measurement of protease activity using thin membrane comprising gelatin and hardening agent A frozen stomach cancer specimen extracted by surgical operation was sliced at −25° C. into a slice having a thickness of 4 μm by using an apparatus for preparing frozen sections and adhered to a crosslinked gelatin thin membrane disclosed in WO97/32035. The used gelatin has a membrane thickness of 7 μm, crosslinked with 1,2-bis(vinylsulfonylacetamido)ethane, and coated on a PET film having a thickness of 175 μm. This gelatin membrane to which the frozen slice was adhered was incubated at 37° C. for 16 hours under 100% of relative humidity, and then air-dried. As a staining solution, a solution was used which was obtained by mixing a solution in which Ponceau 3R was dissolved at a concentration of 0.8% in 5% acetic acid aqueous solution and ethanol at a volume ratio of 3:7. The membrane was immersed in the solution at room temperature for 4 minutes for staining.

After the membrane was washed with water for 10 minutes, the membrane was immersed in a Mayer's hematoxylin solution for 2 minutes for nuclear staining, washed with water for 10 minutes, immersed in ethanol for 20 seconds, and then air-dried. After the drying, a Cover Aid Film (Sakura Seiki Co., Ltd.) was adhered to the membrane with xylene so that the film covered the tissue slice to encapsulate the stomach cancer slice. When this film was held on a plastic mount and observed under an optical microscope, gelatin digestion was observed at sites contacting with the stomach cancer tissue slice where the cancer cells were considered to be present based on the morphology of the nuclei, and thus presence of protease activity was verified. However, the stomach cancer slice present on the gelatin membrane was also stained with Ponceau, and for this reason, a part of traces of digestion was covered with the slice, and area and degree of digestion were not clear.

According to the methods of the present invention, protease activity can be accurately measured, and in addition, morphological observation of tissues and cells on a thin membrane can be easily performed. In particular, since staining process of the thin membrane becomes unnecessary, the operation for measurement is simple, and tissues or cells on the thin membrane are not stained. Therefore, expression of protease activity can be analyzed more precisely.

What is claimed is:

1. A method for measuring protease activity, which comprises the steps of:
   (1) bringing a biosample containing a protease into contact with a crosslinked and/or substantially water-insoluble thin membrane that is formed on a support surface and contains at least one colorant selected from the group consisting of an emulsion-dispersed colorant and a solid-dispersed colorant, wherein said colorant is not a fluorescent colorant, and a protease substrate; and
   (2) washing the thin membrane with an aqueous medium and detecting traces of digestion formed on the thin membrane by the action of the protease.

2. A method for measuring protease activity, which comprises the steps of:
   (1) bringing a biosample containing a protease into contact with a crosslinked and/or substantially water-insoluble thin membrane that is formed on a support surface and contains at least one colorant selected from the group consisting of an emulsion-dispersed colorant and a solid-dispersed colorant and a protease substrate;
   (2) washing the thin membrane with an aqueous medium and detecting traces of digestion formed on the thin membrane by the action of the protease; and
   (3) staining the biosample on the thin membrane.

3. A method according to claim 2, wherein cell nucleus staining is performed as the staining of the biosample.

4. The method according to claim 3, wherein hematoxylin or Methyl Green is used for the staining.

5. A method for measuring protease activity, which comprises the steps of:
   (1) bringing one of two or more substantially continuous slices of a biosample into contact with a crosslinked and/or substantially water-insoluble thin membrane that is formed on a support surface and contains at least one colorant selected from the group consisting of an emulsion-dispersed colorant and a solid-dispersed colorant, wherein said colorant is not a fluorescent colorant, and a protease substrate;
   (2) bringing another slice of said slices into contact with a crosslinked and/or substantially water-insoluble thin membrane that is formed on a support surface and contains at least one colorant selected from the group consisting of an emulsion-dispersed colorant and a solid-dispersed colorant, wherein said colorant is not a fluorescent colorant, a protease substrate, and a protease inhibitor;

(3) washing the thin membranes with an aqueous medium and detecting traces of digestion formed on the thin membranes by the action of the protease; and (4) comparing the traces of digestion on the thin membrane used in the step (1) with the traces of digestion on the thin membranes used in the step (2).

6. A method for measuring protease activity, which comprises the steps of:

(1) bringing one of two or more substantially continuous slices of a biosample into contact with a crosslinked and/or substantially water-insoluble thin membrane that is formed on a support surface and contains at least one colorant selected from the group consisting of an emulsion-dispersed colorant and a solid-dispersed colorant and a protease substrate;

(2) bringing another slice of said slices into contact with a crosslinked and/or substantially water-insoluble thin membrane that is formed on a support surface and contains at least one colorant selected from the group consisting of an emulsion-dispersed colorant and a solid-dispersed colorant, a protease substrate, and a protease inhibitor;

(3) washing the thin membranes with an aqueous medium and detecting traces of digestion formed on the thin membranes by the action of the protease;

(4) staining the biosample on the thin membranes; and (5) comparing the traces of digestion on the thin membrane used in the step (1) with the traces of digestion on the thin membrane used in the step (2).

7. The method according to claim 6, wherein cell nucleus staining is performed as the staining of the biosample.

8. The method according to claim 7, wherein hematoxylin or Methyl Green is used for the staining.

9. The method according to any one of claims 1–6 or 7–8, wherein the biosample is a tissue, a cell, or a body fluid obtained from a mammal including a human.

* * * * *